US011134983B1

(12) United States Patent
Quintero

(10) Patent No.: US 11,134,983 B1
(45) Date of Patent: Oct. 5, 2021

(54) OBTURATOR AND CANNULA FOR UTERINE AND FETAL SURGERIES

(71) Applicant: Ruben Quintero, Coral Gables, FL (US)

(72) Inventor: Ruben Quintero, Coral Gables, FL (US)

( * ) Notice: Subject to any disclaimer, the term of this patent is extended or adjusted under 35 U.S.C. 154(b) by 0 days.

(21) Appl. No.: 17/199,137

(22) Filed: Mar. 11, 2021

Related U.S. Application Data

(62) Division of application No. 16/837,455, filed on Apr. 1, 2020.

(51) Int. Cl.
| | | |
|---|---|---|
| *A61B 17/34* | (2006.01) | |
| *A61B 17/42* | (2006.01) | |
| *A61M 25/09* | (2006.01) | |
| *A61M 29/00* | (2006.01) | |
| *A61B 17/00* | (2006.01) | |

(52) U.S. Cl.
CPC .... *A61B 17/3423* (2013.01); *A61B 17/00234* (2013.01); *A61B 17/3496* (2013.01); *A61B 17/42* (2013.01); *A61B 17/4208* (2013.01); *A61M 25/09* (2013.01); *A61M 29/00* (2013.01); *A61B 2017/4216* (2013.01); *A61M 2210/145* (2013.01); *A61M 2210/1425* (2013.01)

(58) Field of Classification Search
CPC .................. A61B 17/4208; A61B 10/0048
See application file for complete search history.

(56) References Cited

U.S. PATENT DOCUMENTS

| | | | | |
|---|---|---|---|---|
| 4,280,508 A * | 7/1981 | Barrada | ............ | A61B 10/0048 374/155 |
| 4,308,875 A * | 1/1982 | Young | ............... | A61B 17/4208 600/566 |
| 5,147,335 A * | 9/1992 | Wright | ............... | A61B 10/0048 600/576 |
| 5,279,570 A * | 1/1994 | Dombrowski | ..... | A61B 10/0048 604/164.01 |
| 5,951,497 A * | 9/1999 | Wallace | ................. | A61B 5/035 600/587 |
| 8,348,903 B2 * | 1/2013 | Baplue | ................. | A61N 5/1007 604/195 |
| 2008/0071297 A1 * | 3/2008 | Kohl | ................. | A61B 17/0483 606/151 |
| 2011/0264098 A1 * | 10/2011 | Cobbs | ................ | A61B 17/7097 606/93 |
| 2014/0336600 A1 * | 11/2014 | Harrell | ............... | A61B 10/0048 604/319 |
| 2015/0272618 A1 * | 10/2015 | Fung | .................. | A61B 17/3417 606/185 |
| 2015/0342635 A1 * | 12/2015 | Tsamir | ............... | A61B 17/3494 604/506 |

* cited by examiner

*Primary Examiner* — Jenna Zhang
(74) *Attorney, Agent, or Firm* — Mark Terry

(57) ABSTRACT

A trocar assembly and method for uterine and fetal surgeries includes a cannula defining a hollow tubular sleeve that extends from a first open end to a second open end, a hollow obturator defining a shaft that extends from a first open end that is tapered to a second open end, wherein the hollow obturator is located within the cannula, and wherein the trocar assembly is configured to be inserted into a patient's body to give access to a bodily cavity, such as the amniotic cavity or the fetus. The trocar assembly is configured for insertion into the amniotic cavity using the Seldinger technique.

5 Claims, 9 Drawing Sheets

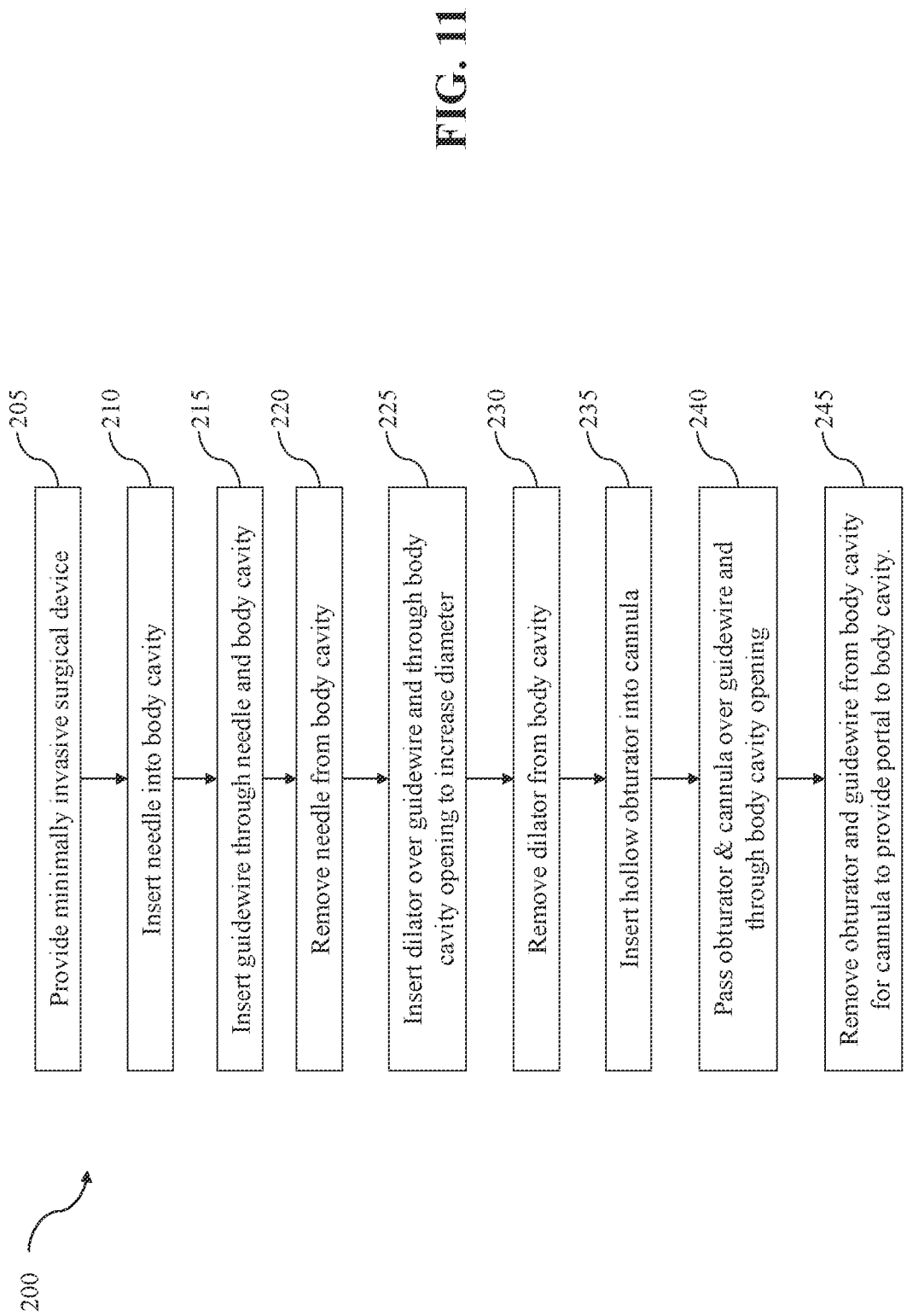

OBTURATOR AND CANNULA FOR UTERINE AND FETAL SURGERIES

CROSS-REFERENCE TO RELATED APPLICATIONS

This patent application is a divisional of patent application Ser. No. 16/837,455 filed Apr. 1, 2020. The subject matter of patent application Ser. No. 16/837,455 is hereby incorporated by reference in its entirety.

STATEMENT REGARDING FEDERALLY SPONSORED RESEARCH OR DEVELOPMENT

Not applicable.

INCORPORATION BY REFERENCE OF MATERIAL SUBMITTED ON A COMPACT DISC

Not applicable.

TECHNICAL FIELD

The claimed embodiments relate to the field of minimally invasive surgical devices, and more specifically to the field of minimally invasive surgical instruments for entry into the pregnant uterine cavity (amniotic cavity) and the fetus.

BACKGROUND

Globally, 15 million laparoscopic (minimally invasive surgeries) surgeries are performed every year, growing at a rate of 8.3%. A minimal incision is made to insert a port-like device, i.e. a trocar, to gain access to the inner body cavity. The trocar is placed through the abdomen and used to aid insufflating the abdominal cavity (pneumoperitoneum). Operations are then performed by passing medical devices and tools such as a laparoscope and stapler through the cannula of the trocars. The global trocar market is 1.4 billion dollars, with 32% of the market share (450 million) consumed by the United States.

Laparoscopic surgery presents a unique and intricate safety challenge, compared to conventional surgery, as it is a more demanding specialty with technology-dependent complex applications with poor redundancy. Laparoscopists are expected to perform flawlessly, in a distorted proprioceptive environment, where depth perception, tactile feedback and other important intuitive fundamentals of conventional surgery are lacking. Surgeons are aware of the potential dangers during surgery, especially those associated with using conventional trocar methods.

The most significant risks are from trocar injuries during insertion into the abdominal cavity when a significant amount of force must be applied to the trocar to penetrate the abdominal wall. Each patient and circumstance require a different amount of force to be applied for trocar insertion. Moreover, it requires skill and experience on the part of the surgeon to insert the trocar with sufficient force to penetrate the abdominal cavity, while still maintaining enough control to stop the movement of the trocar once the abdominal wall has been traversed. For example, too much force may accidentally propel the trocar into a blood vessel or puncture an internal organ such as the large intestine, and blood vessel hemorrhage or life-threatening bacterial infections may result. Therefore, the safety margin between the force required for trocar insertion and trocar injury is thin, especially during pediatric surgery and fetal surgery.

In endoscopic fetal surgery, the surgeon needs to access the amniotic cavity or the fetus. Ultrasound is used to guide safe entry into the uterus. Entry into the uterus is done directly via a solid trocar or indirectly, using the Seldinger technique. Direct trocar entry is limited by the diameter of the trocar, because the force needed to traverse the uterus can be prohibitively unsafe. Indirect entry into the uterus using a Seldinger technique requires the use of dilators, which are not integral with the cannula. Insertion of a cannula with the use of a dilator can result in unintentional injury from the dilator to the distal tissues, as there is no mechanism to prevent the dilator from advancing beyond the desired depth.

Direct trocar entry into the amniotic cavity of the pregnant uterus or the fetus can be typically performed without much force with small trocars. For larger trocars, more force is necessary, but direct trocar entry is still possible. For large trocars, direct trocar entry into the amniotic cavity or the fetus requires an amount of force by the surgeon that can be unsafe. For some of the more complicated endoscopic fetal surgical procedure done today, the surgeon must use a wide array of larger instruments inside the amniotic cavity or the fetus. A conventional trocar cannot be inserted directly into the uterus or the fetus because the trocar is too wide, and the force needed to insert it into the amniotic cavity, or the fetus is too much and unsafe. It is not desirable that excessive force be required to enter into such a delicate area during fetal surgery.

With over 15 million laparoscopic surgeries being performed annually, the need for safe and efficient, minimally invasive surgical tools is significant. Therefore, a need exists to improve over the prior art and more particularly, for a minimally invasive surgical system for entry into the uterine cavity.

SUMMARY

A minimally invasive surgical system and method is disclosed. This Summary is provided to introduce a selection of disclosed concepts in a simplified form that are further described below in the Detailed Description including the drawings provided. This Summary is not intended to identify key features or essential features of the claimed subject matter. Nor is this Summary intended to be used to limit the claimed subject matter's scope.

In one embodiment, a trocar assembly for minimally invasive surgeries includes a cannula defining a hollow tubular sleeve that extends from a first open end to a second open end, a hollow obturator defining a shaft that extends from a first open end that is tapered to a second open end, wherein the hollow obturator is located within the cannula, and wherein the trocar assembly is configured to be inserted into a patient's body to give access to a bodily cavity, such as the amniotic cavity or the fetus. The trocar assembly is configured for insertion into the amniotic cavity using the Seldinger technique.

In another embodiment, a minimally invasive surgical system for uterine and fetal surgeries is disclosed. The system includes an 18-gauge hypodermic needle defining a hollow shaft that extends from a first open end to a second open end having an outer diameter of 1.2 mm, wherein the first end of the hypodermic needle is configured to create an opening into an amniotic cavity of a patient, a guidewire defining a first end and a second end, wherein the first end is configured to be inserted into the second open end of the hypodermic needle such that the first end of the guidewire extends through the first open end of the 18-gauge hypodermic needle into the amniotic cavity, and wherein the second end of the guidewire is configured to remain outside of the patient's body. The system further includes a trocar assembly comprising a cannula defining a hollow tubular sleeve that extends from a first open end to a second open end, and a hollow obturator defining a shaft that extends from a first open end that is tapered to a second open end, wherein the hollow obturator is located within the cannula, wherein the first open end of the obturator is configured for inserting the second end of the guidewire, and wherein the trocar assembly is configured for insertion into the amniotic cavity using the guidewire as a guide In another embodiment, a method for performing minimally invasive uterine and fetal surgical procedures is disclosed. The method includes providing a device comprising a hypodermic needle defining a hollow shaft that extends from a first open end to a second open end, a guidewire defining a first end and a second end, and a trocar assembly comprising, a cannula defining a hollow tubular sleeve that extends from a first open end to a second open end and, a hollow obturator defining a shaft that extends from a first open end that is tapered to a second open end, wherein the hollow obturator is located within the cannula. The method further includes inserting the first open end of the needle through a patient's skin and into an amniotic cavity so as to create an opening, inserting the first end of the guidewire through the second open end of the needle and into the amniotic cavity, removing the needle from the amniotic cavity such that the first end of the guidewire remains inside the amniotic cavity and the second end of the guidewire remains outside of the patient's body, inserting the first open end of the obturator into the second open end of the cannula such that the first open end of the obturator protrudes from the first open end of the cannula, passing the first open end of the obturator and the first open end of the cannula over the second end of the guidewire and inserting the trocar assembly into the amniotic cavity using the guidewire as a guide, and removing the obturator and the guidewire from the amniotic cavity such that the first open end of the cannula remains inside the amniotic cavity and the second open end of the cannula remains outside of the patient's body to provide a portal to the amniotic cavity.

Additional aspects of the disclosed embodiment will be set forth in part in the description which follows, and in part will be obvious from the description, or may be learned by practice of the disclosed embodiments. The aspects of the disclosed embodiments will be realized and attained by means of the elements and combinations particularly pointed out in the appended claims. It is to be understood that both the foregoing general description and the following detailed description are exemplary and explanatory only and are not restrictive of the disclosed embodiments, as claimed.

BRIEF DESCRIPTION OF THE DRAWINGS

The accompanying drawings, which are incorporated in and constitute part of this specification, illustrate claimed embodiments and together with the description, serve to explain the principles of the disclosed embodiments. The embodiments illustrated herein are presently preferred, it being understood, however, that the invention is not limited to the precise arrangements and instrumentalities shown, wherein:

FIG. 11 is a flowchart describing the steps of the process for performing minimally invasive surgical procedures, according to an example embodiment.

DETAILED DESCRIPTION

Figure 3:
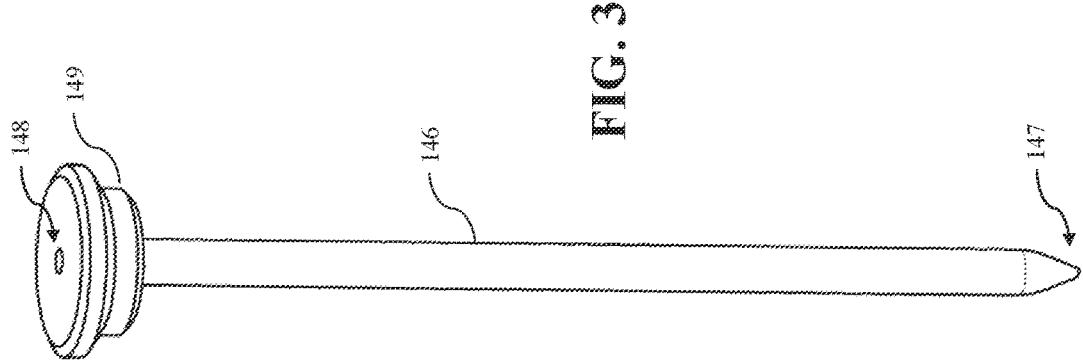
FIG. 3 is a perspective view of a hollow obturator, according to an example embodiment.

The following detailed description refers to the accompanying drawings. Whenever possible, the same reference numbers are used in the drawings and the following description to refer to the same or similar elements. While disclosed embodiments may be described, modifications, adaptations, and other implementations are possible. For example, substitutions, additions or modifications may be made to the elements illustrated in the drawings, and the methods described herein may be modified by substituting reordering or adding additional stages or components to the disclosed methods and devices. Accordingly, the following detailed description does not limit the disclosed embodiments. Instead, the proper scope of the disclosed embodiments is defined by the appended claims.

The claimed embodiments improve upon the prior art by providing a minimally invasive surgical system for entry of a trocar assembly into the uterine cavity by means of the Seldinger technique. The system is configured to safely allow access to the uterine cavity (amniotic cavity) without the need to apply much force during insertion into the uterine cavity. The claimed embodiments provide ease of access to the uterine cavity (amniotic cavity) (or other organ or cavity), such that larger diameter trocars can be used, as well as more control in the deployment of the trocar assembly by limiting the depth to which the trocar tip can be advanced into the patient.

More specifically, the claimed embodiments provide a surgical trocar device having a hollow obturator and cannula that requires less force to insert into the uterine cavity (amniotic cavity). The obturator is hollow to allow insertion of the trocar assembly using the Seldinger technique. The hollow obturator is designed to minimize tissue damage and insertion effort by providing a smooth, unencumbered surface transition using the Seldinger technique. The cavity is first accessed with a thin-gauge needle. A guidewire is passed through the needle and the needle is removed, leaving the guidewire in place. The trocar assembly with the hollow obturator is passed over the guidewire into the cavity and the guidewire is removed, after which the obturator is removed. A resilient sealing element within the cannula minimizes the escape of fluid or gas after removal of the obturator.

The claimed embodiments allow for the surgeon to use enough force to enter the uterine cavity but while still maintaining enough control to stop the movement of the trocar once the abdominal wall has been traversed. The claimed embodiments also allow for the surgeon to control his/her movement to prevent accidental damage to the patient's body. The claimed embodiments further allow for the surgeon to utilize a safe amount of force (i.e., not excessive) while traversing the uterus, so as to prevent unintentional injury during uterine and fetal surgeries.

By way of background, a trocar, is a surgical device used to obtain access to a body cavity to perform various surgical procedures, for example, laparoscopic surgery or arthroscopic surgery. The trocar is an elongated, pointed surgical instrument having a pointed rod-like device, referred to in the art as an "obturator", that is fitted into a tube-like device that is referred to in the art as a "cannula". The pointed, sometimes sharply pointed, end of the obturator projects out the end of the cannula and is used to penetrate the outer tissue of the cavity. After the tissue is penetrated and the body cavity, for example, is accessed by the trocar, the obturator is withdrawn from the cavity and the cannula is left in place in the cavity to provide a channel for accessing the cavity. The body cavity can then be accessed by further surgical instruments via the cannula to perform various surgical procedures, or the cannula can simply be used as a drainage outlet. Among other uses, trocar devices are typically used to penetrate the human abdominal wall to gain access, for example, to the organs within.

The Seldinger technique, also known as the Seldinger wire technique, is a medical procedure to obtain safe access to blood vessels and other hollow organs. The Seldinger technique is performed with the aid of a guidewire. The procedure starts by using a needle to first enter the body cavity (e.g., blood vessel) which the surgeon desires to access. Then, a guidewire is inserted through the needle, and the needle is removed, with the guidewire remaining in place. A blunt cannula or dilator is then passed over the guidewire to allow the insertion of a catheter or other device that is larger in diameter than the needle used to access the vessel. The cannula or dilator is usually hollow to allow its use over the guidewire and is typically tapered at the end. The purpose of the tapered-end dilator is to increase the diameter of the opening made by the needle using the guidewire as a path. Once the opening is dilated to a desired diameter, an additional element, such as a balloon or catheter or balloon can be inserted. The Seldinger technique is typically used to obtain safe access to small bodily cavities such as the interior of blood vessels and other small hollow organs.

Referring now to the Figures, FIGS. 1-5 illustrate a minimally invasive surgical system for entry into the uterine cavity 101 according to an example embodiment and will be discussed together for ease of reference. Note that this document refers to the uterine cavity, the claimed embodiment can be used to enter any bodily cavity, organ or a fetus.

Figure 4:
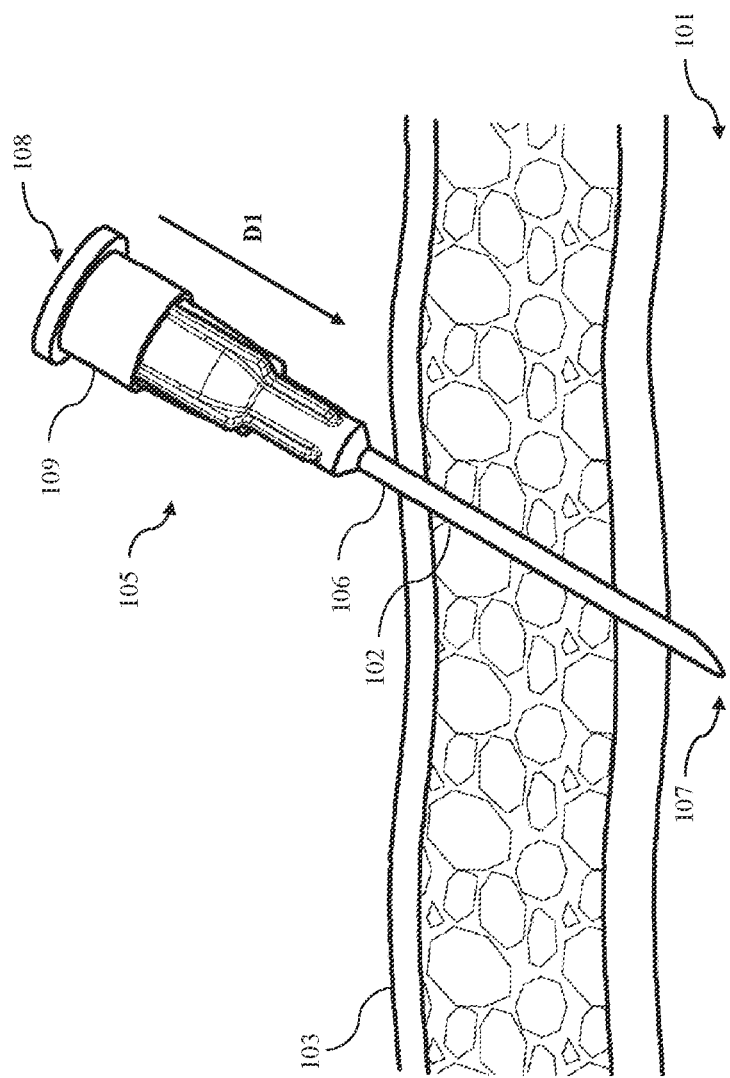
FIG. 4 is a perspective side view of a needle pierced into a body cavity, according to an example embodiment.

The system includes a needle 105 defining a hollow shaft 106 that extends from a first open end 107 to a second open end 108. The first end 107 of the needle is beveled to form a sharp point to puncture into skin. The second end 108 of the needle includes a hub 109 for mounting the needle onto a conventional syringe (not shown). As best illustrated in FIG. 4, in operation, the needle is pierced through the patient's skin and into the uterine cavity (in the direction of arrowed line D1) to create an opening 102 into the uterine cavity 101. In one embodiment, the needle 105 comprises an 18-gauge hypodermic needle having an outer diameter of 1.2 mm. It should be appreciated that the depending on the surgical procedure, the diameter of both the inside and outside of the needle may be increased or decreased. Additionally, the length of the needle may vary according to the depth the needle must penetrate. The needle may be comprised of materials such as titanium, 316L steel, 304 steel, or any other suitable material known in the art.

Figure 5:
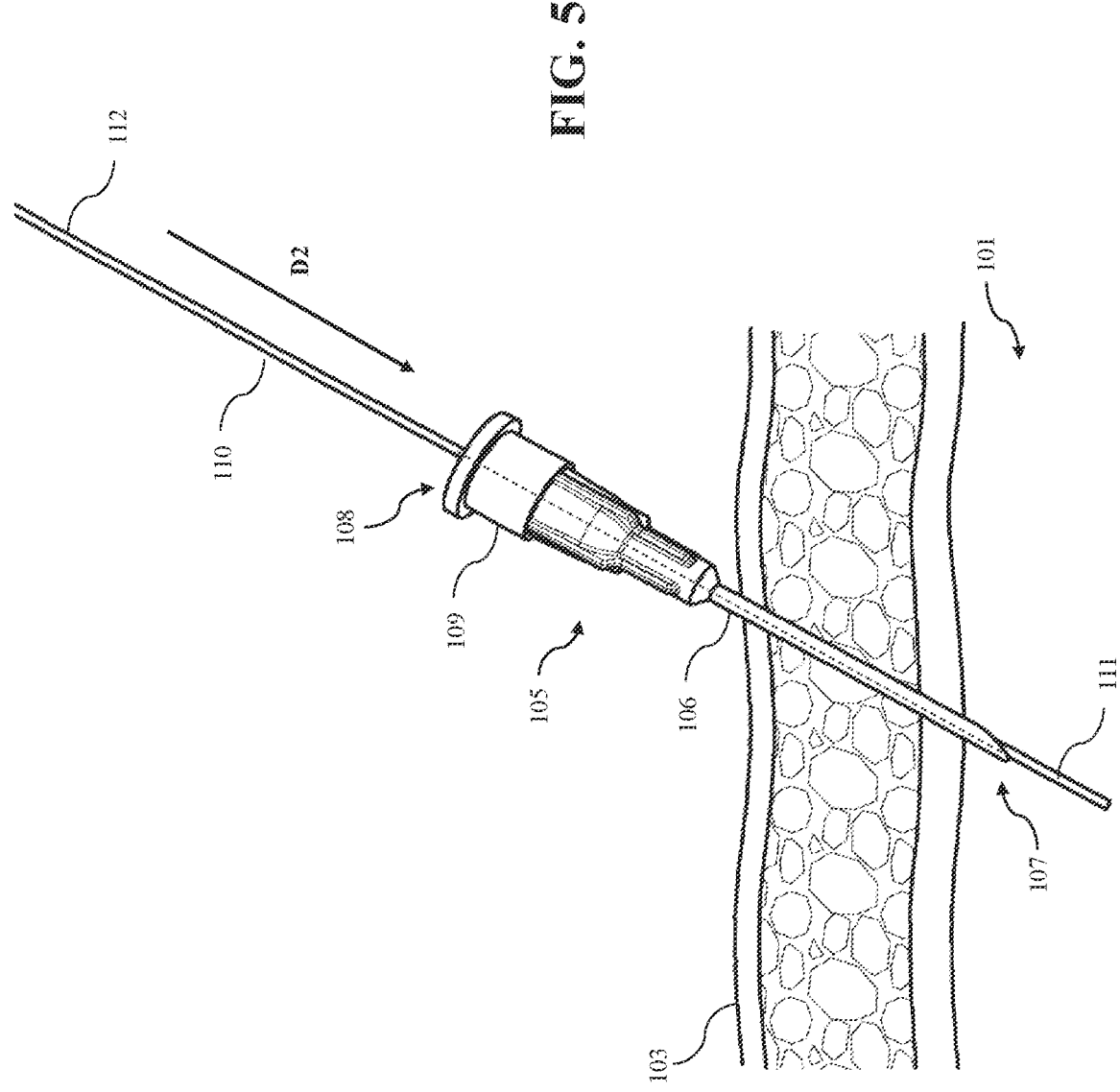
FIG. 5 is a perspective side view of a needle pierced into a body cavity, wherein a first end of a guidewire is inserted through a second open end of the needle and into the body cavity, according to an example embodiment.
Figure 6:
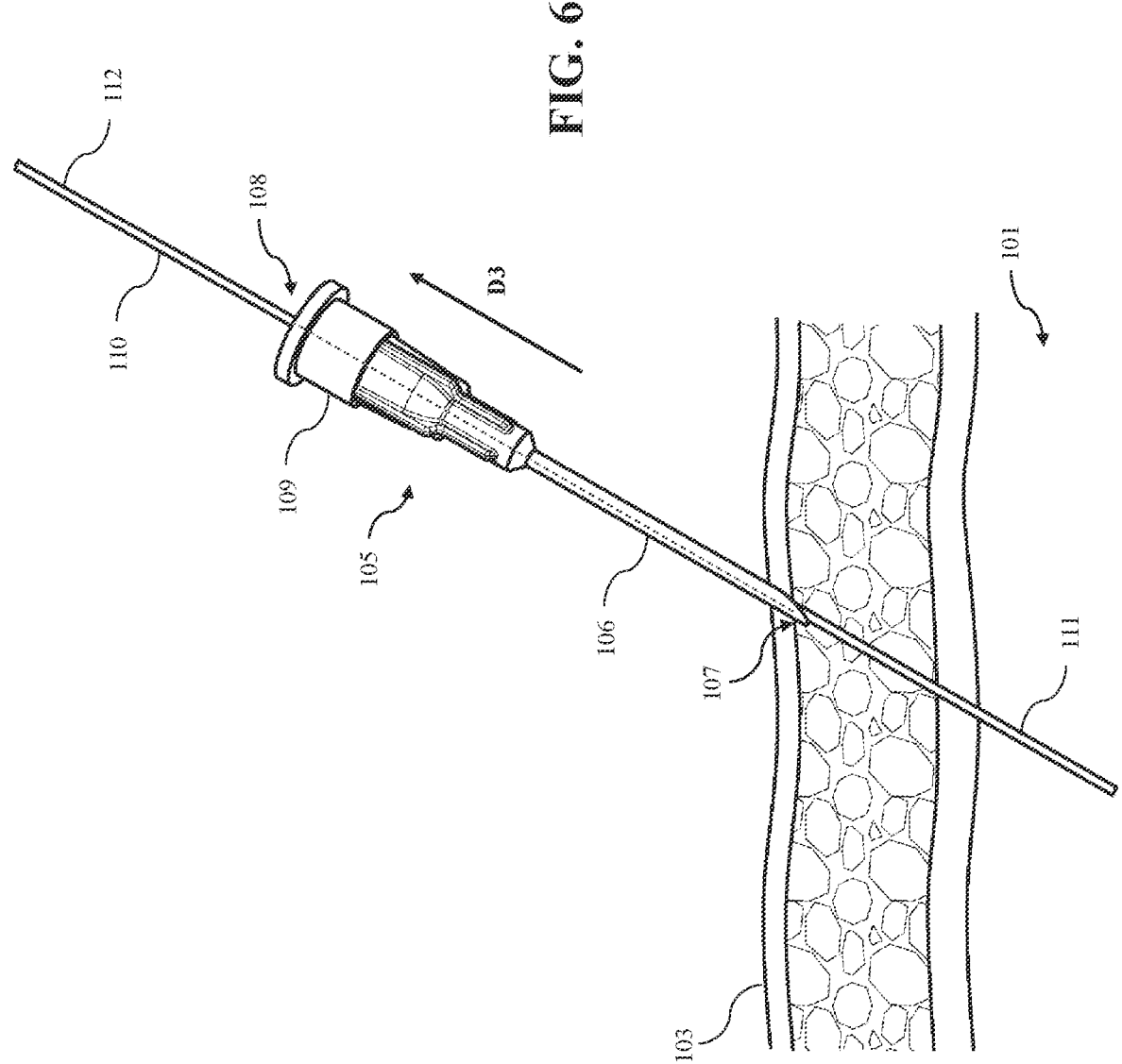
FIG. 6 is a perspective side view of a needle being removed from a body cavity, wherein a first end of a guidewire remains inside the body cavity, according to an example embodiment.

The system further includes a guidewire 110 that is configured to safely allow entry into the uterine cavity by means of the Seldinger technique. In operation, as best illustrated in FIG. 5, a first end 111 of the guidewire 110 is inserted (in the direction of arrowed line D2) into the second open end 108 of the needle 105 such that the first end 111 of the guidewire 110 extends through the first open end 107 of the needle 105 into the uterine cavity 101 and a second end 112 of the guidewire 110 remains outside of a patient's body. As best illustrated in FIG. 6, once the guidewire is securely positioned inside the uterine cavity, the needle is removed from the uterine cavity (in the direction of arrowed line D3) such that the first end of the guidewire remains inside the uterine cavity and the second end of the guidewire remains outside of the patient's body. It should be appreciated that the guidewire may vary in diameter, length, coatings and position indicators (marked or unmarked), and such variations are within the spirit and scope of the claimed embodiments. The guidewire may be comprised of any number of hardened material(s) or steel alloys such as hardened materials and alloys of high carbon steel, or stainless steel alloy, or such as spring hardened stainless steel, including for example, piano wire or any of the stainless steel alloys, or any other suitable material known in the art, and such variations are within the spirit and scope of the claimed embodiments.

Figure 1:
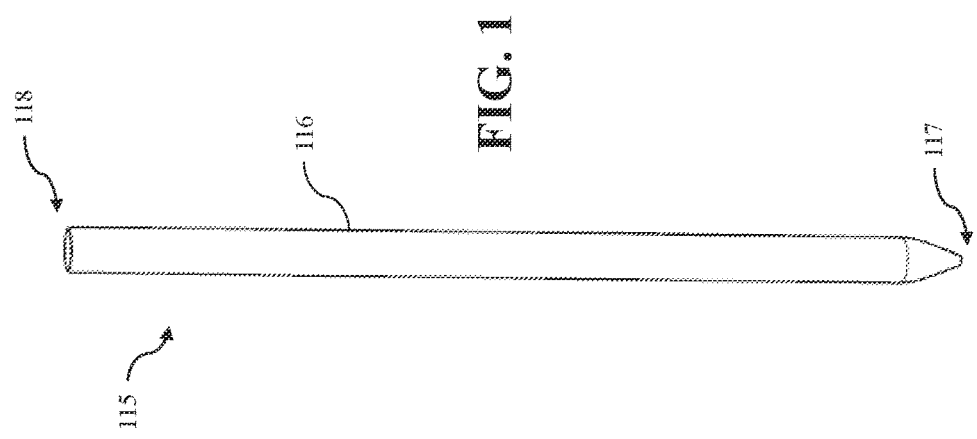
FIG. 1 is a perspective view of a dilator, according to an example embodiment.

As illustrated in FIG. 1, the system further includes at least one dilator 115 defining a cylindrical shaped body. A dilator is used to induce dilation, that is, to expand an opening or passage into a body cavity. The at least one dilator includes a tapered hollow shaft 116 that extends from a first open end 117 to a second open end 118. In one embodiment, the first open end 117 of the at least one dilator includes a blunt tip to prevent inadvertent puncture or tearing of abdominal structures. The at least one dilator 115 is gripped or handled by a hand of a user during surgical procedures by grabbing the surface of the dilator.

Figure 7:
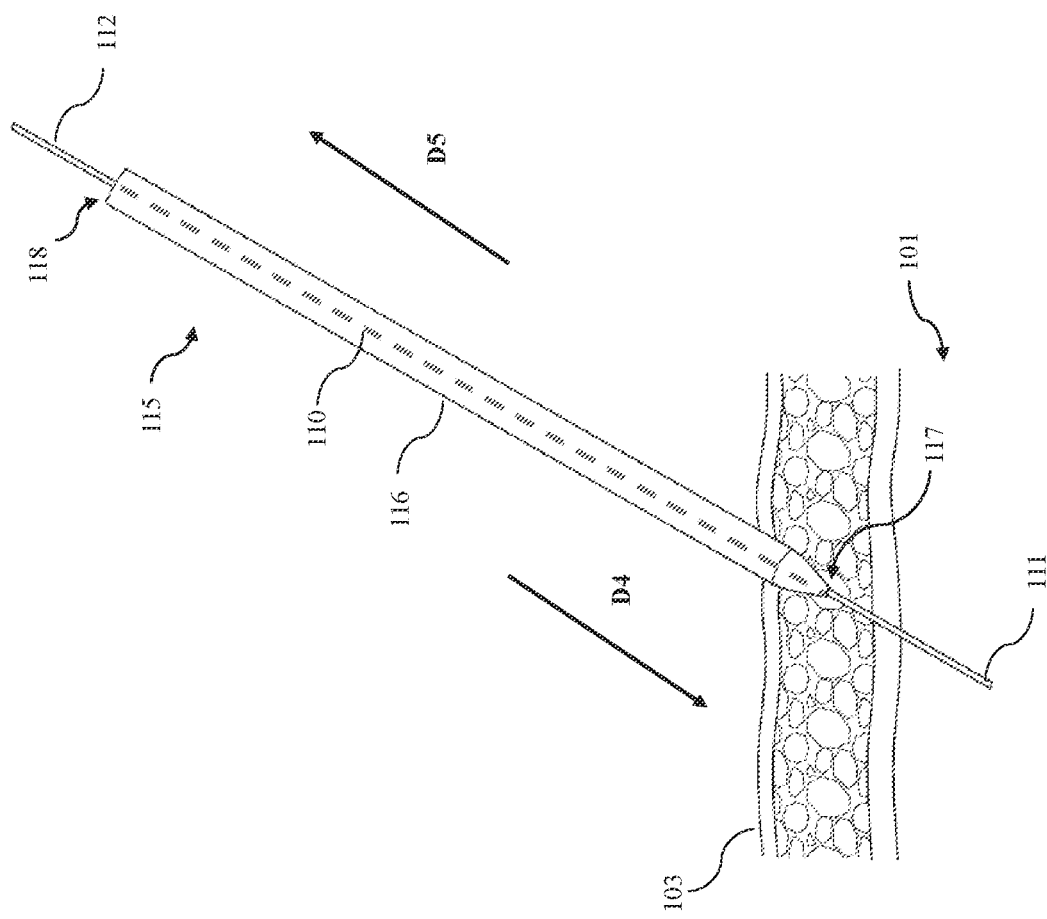
FIG. 7 is a perspective side view of a first open end of a dilator passed over a second end of a guidewire, wherein the dilator is entering the body cavity opening, according to an example embodiment.

In operation, as best illustrated in FIG. 7, the first open end 117 of the at least one dilator 115 is inserted over the second end 112 of the guidewire 110 and into the uterine cavity 101 (in the direction of arrowed line D4) to separate and dilate the diameter of the opening into the uterine cavity 101 made by the needle. In one embodiment, additional dilators of gradually increasing size may be successively advanced over the second end of the guidewire and through the uterine cavity opening to increase the diameter of the opening into the uterine cavity 101 made by the needle. Once the uterine cavity opening is sufficiently dilated, the at least one dilator is removed from the uterine cavity (in the direction of D5) such that the first end of the guidewire remains inside the body cavity and the second end of the guidewire remains outside of the patient's body. It should be appreciated that the at least one dilator may vary in shape, diameter, length, and coatings, and such variations are within the spirit and scope of the claimed embodiments. The at least one dilator may be comprised of materials such as stainless steel, Teflon, polyethylene, plastic, or any other suitable material known in the art. It should further be noted that typical dilators do not include a stopper or cap on its distal end, thereby allowing for the dilator to fully enter into the bodily in an unfettered fashion. This feature has led to some problems during surgeries where the dilator is mistakenly pushed too far into the bodily cavity and can cause damage or injury to the patient.

Figure 2:
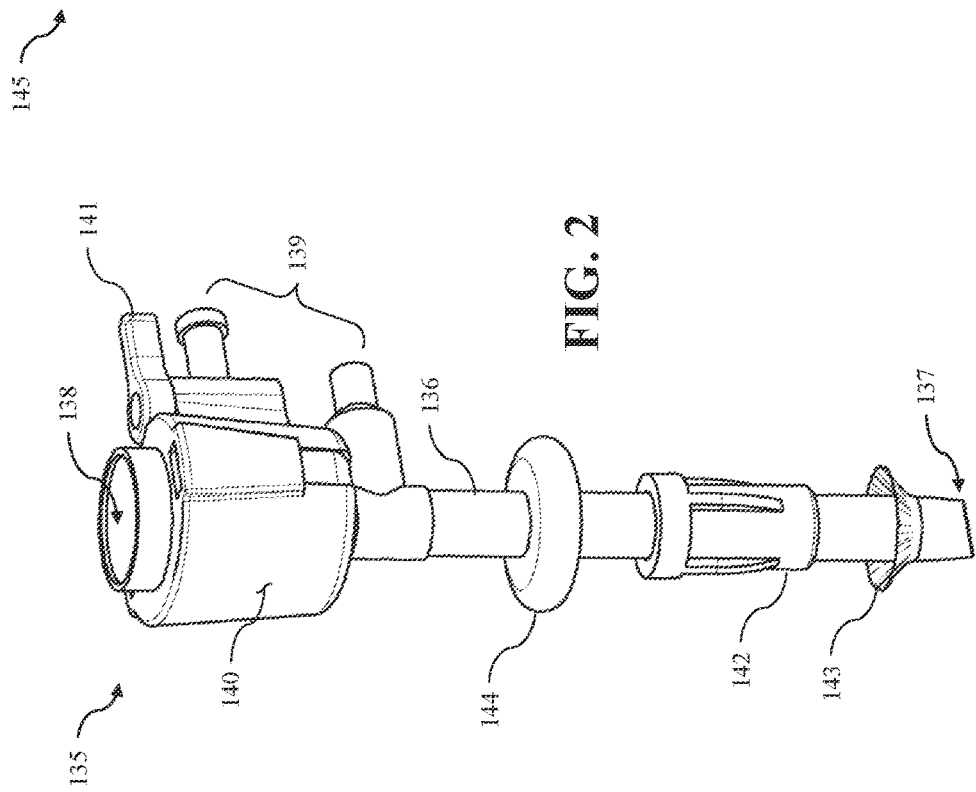
FIG. 2 is a perspective view of a cannula, according to an example embodiment.

The system further includes a trocar assembly 125 comprising a cannula 135 and a hollow obturator 145 configured to be inserted into a patient's body to give access to the uterine cavity 101. The cannula 135 is configured to provide a portal to the uterine cavity 101 to allow instrument insertion and exchange during surgical procedures. As best shown in FIG. 2, the cannula 135 includes a hollow tubular sleeve 136 that extends from a first open end 137 to a second open end 138. The outer diameter of the hollow tubular sleeve 136 of the cannula 135 is sufficiently sized to safely allow insertion into the uterine cavity without applying force. In one embodiment, the hollow tubular sleeve 136 of the cannula 135 comprises an outer diameter of approximately 5 mm. In one embodiment, the hollow tubular sleeve 136 of the cannula 135 comprises an inner diameter of approximately 3.5 mm.

In one embodiment, the second end 138 of the cannula includes a housing component 140. The interior of the housing component includes a valve device (not shown) to seal in an air-tight manner the obturator inserted into the cannula or instruments and the like inserted through the cannula. Additionally, the valve device is used to close the cannula in an air-tight manner when no obturator or instrument is inserted. In one embodiment, the housing component 140 includes an insufflation valve 141 (e.g., a stopcock valve) and at least one Luer connector 139 to introduce an insufflation fluid (e.g. carbon dioxide) through the hollow tubular sleeve 136 of the cannula and subsequently into the uterine cavity to elevate the interior walls of the uterine cavity.

In one embodiment, the cannula includes a threaded anchor 142 slidably engaged on the exterior of the hollow tubular sleeve 136 to secure the cannula in place. In one embodiment, the cannula may be sutured or screwed in place to the uterine wall or held in place by inflatable balls and plastic flanges 143 to prevent migration. In one embodiment, the cannula includes a stop member 144 slidably engaged on the exterior of the hollow tubular sleeve 136. The stop member is configured to be moved against the exterior surface of the abdomen 103 to secure the cannula in place. It should be appreciated that the cannula may vary in shape, diameter, length, and coatings, and such variations are within the spirit and scope of the claimed embodiments. The cannula may be comprised of materials such as stainless steel, silver, silicone, brass, titanium, or any other suitable material known in the art.

Figure 8:
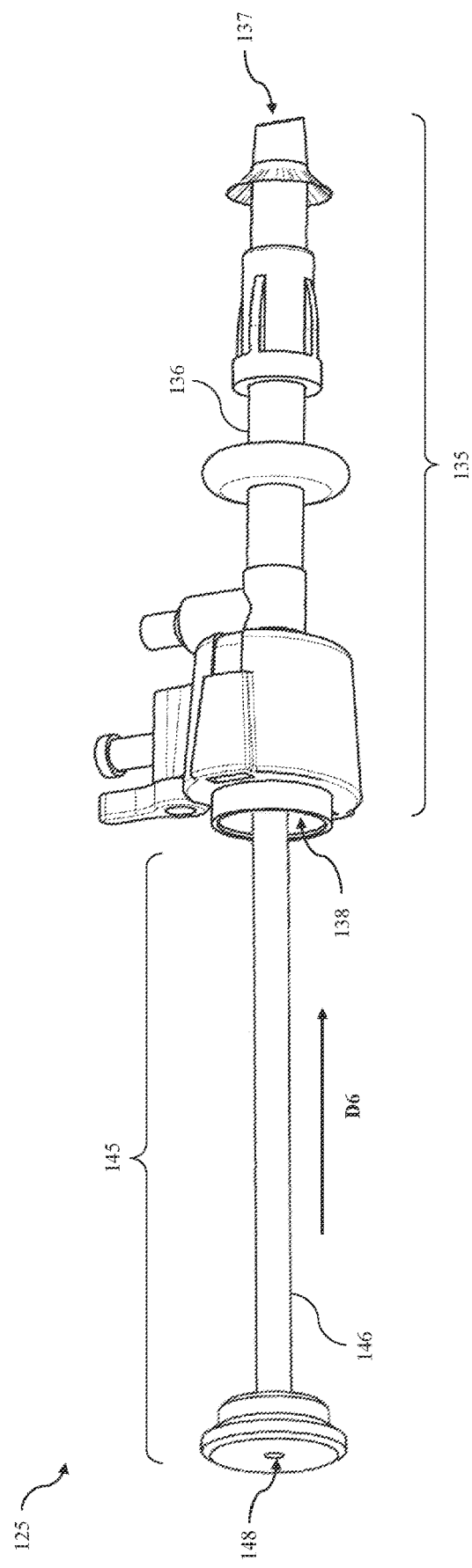
FIG. 8 is a perspective side view of a trocar assembly, wherein a first open end of the hollow obturator is entering a second open end of a cannula, according to an example embodiment.

As best shown in FIG. 3, the obturator 145 defines a hollow shaft 146 that extends from a first open end 147 that is tapered to a second open end 148, which includes a disc. The hollow shaft 146 of the obturator 145 comprises an outer diameter that is smaller than the inner diameter of the hollow tubular sleeve 136 of the cannula 135. As best shown in FIG. 8, the first open end 147 of the obturator 145 is configured to be inserted into the second open end 138 of the cannula 135 (in the direction of arrowed line D6) such that the first open end 147 of the obturator 145 protrudes out of the first open end 137 of the cannula. In one embodiment, the obturator 145 comprises an outer diameter of approximately 5 mm. In another embodiment, the obturator 145 comprises an outer diameter of approximately 3.5 mm.

Figure 9:
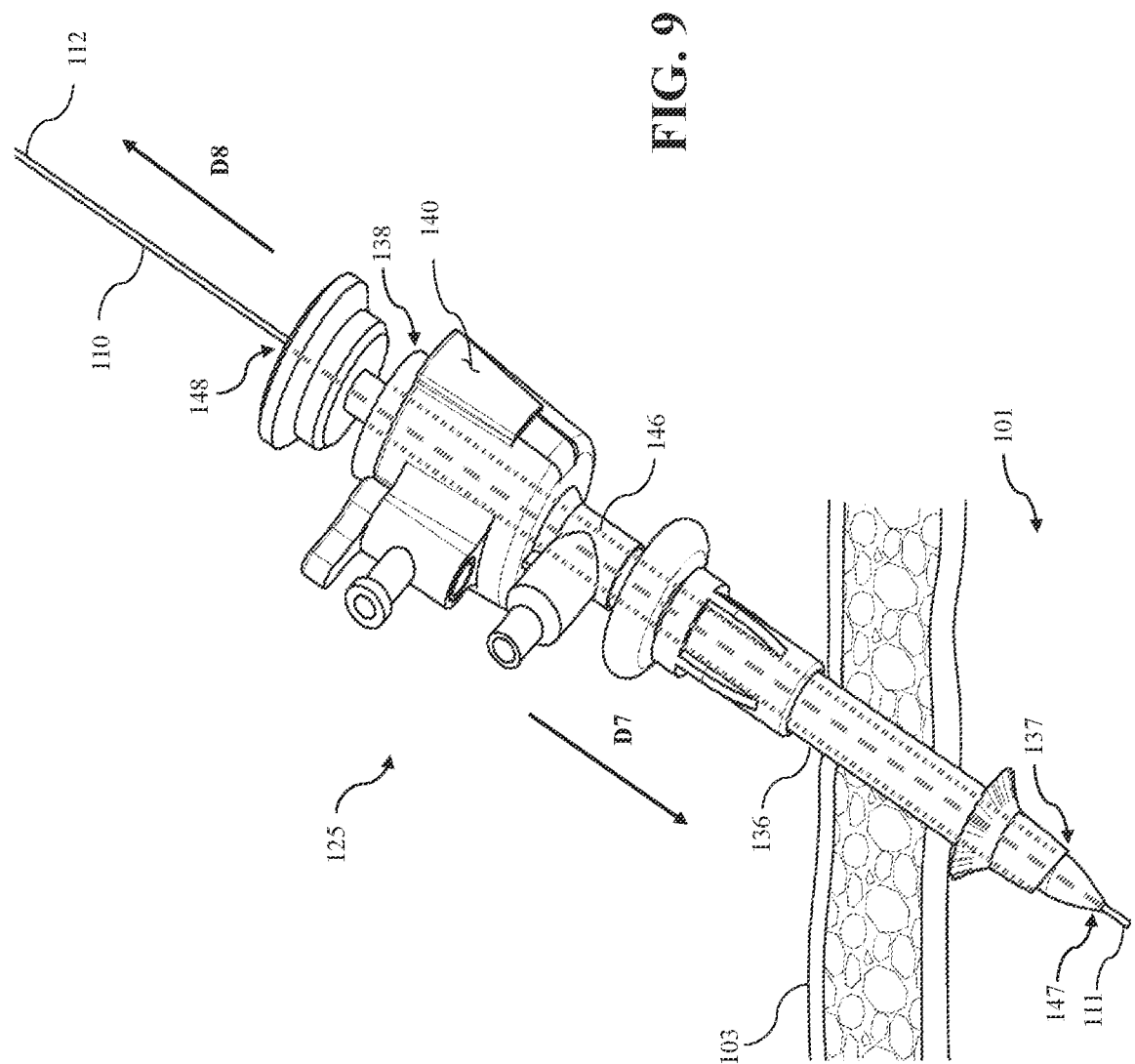
FIG. 9 is a perspective side view of a trocar assembly showing the hollow obturator being passed over a second end of a guidewire inserted into a body cavity opening, according to an example embodiment.

Additionally, the obturator comprises a length that is longer than the length of the cannula 135. In operation, as best shown in FIG. 9, the first open end 147 of the obturator extends through the first open end 137 of the cannula 135 to penetrate the patient's skin and thereby facilitate access to the uterine cavity. It should be appreciated that the obturator may vary in shape, diameter, length, and coatings, and such variations are within the spirit and scope of the claimed embodiments. The obturator, which is an elongated and rigid structure, may be comprised of materials such as stainless steel, silver, silicone, brass, titanium, or any other suitable material known in the art.

The hollow obturator 145 may comprise a disc 149 located at the second open end 148 of the hollow obturator. Note the opening of the second open end 148 is located within the disc. The disc 149 may be used by the surgeon to apply pressure on the obturator using his/her hands and may be used to hold the second open end of the obturator 145 using his/her fingers for better handling of the obturator. Note also that the disc 149 may comprise a combination of two discs—a first disc with a first diameter that is coupled to the second end of the obturator, and a second disc having a second diameter greater than the first diameter, wherein the second disc is located on top of, or distally from, the first disc. The combination of the two discs provide a more ergonomic device for the surgeon to hold the second end of the obturator 145 using his/her thumb on the distal side and forefinger/middle finger on the proximal side.

Figure 10:
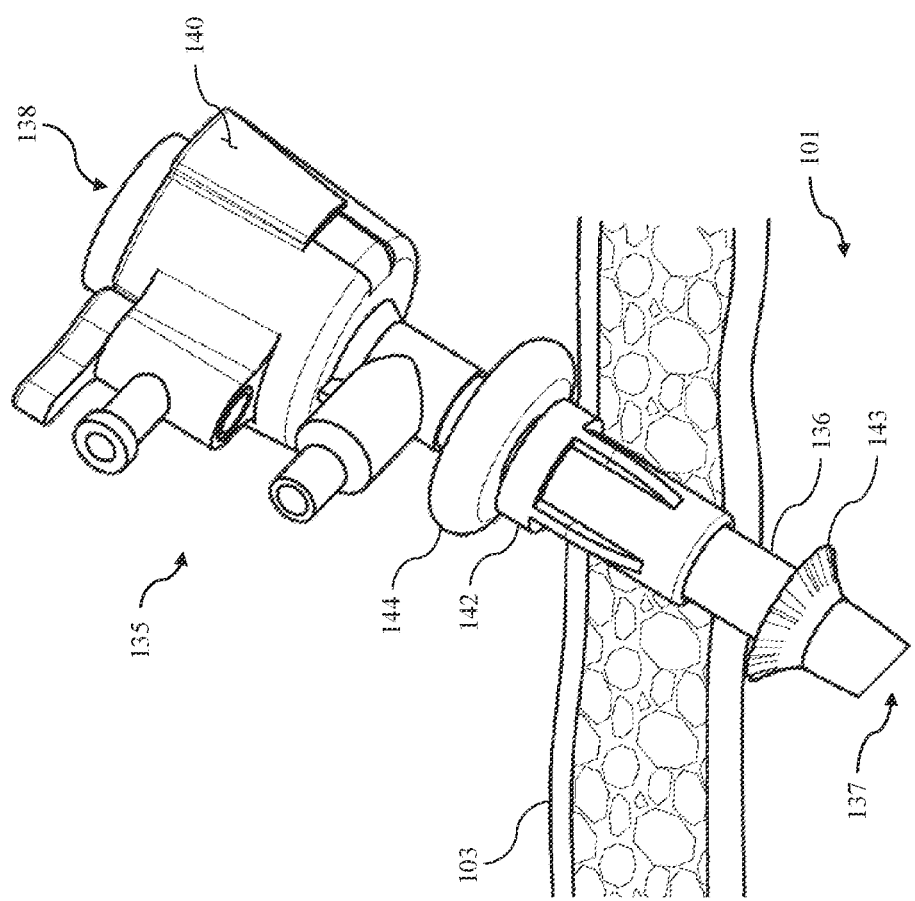
FIG. 10 is a perspective side view of a cannula inserted into a body cavity opening, wherein the guidewire and the obturator have been removed, according to an example embodiment.

In operation, as further shown in FIG. 9, the first open end 117 of the obturator and the first open end 137 of the cannula 135 are passed over the second end 112 of the guidewire and inserted through the opening 102 (in the direction of arrowed line D7) into the uterine cavity 101. That is, the guidewire guides the trocar assembly into the uterine cavity, as in the Seldinger technique. Following insertion of the first open end 117 of the obturator and the first open end 137 of the cannula 135 into the uterine cavity, the guidewire and obturator are removed (in the direction of arrowed line D8). Thereafter, as best shown in FIG. 10, the first open end 137 of the cannula 135 remains inside the uterine cavity 101 and the second open end 138 of the cannula 135 remains outside of the patient's body to provide a portal to the uterine cavity.

FIG. 11 is a flowchart describing the steps of the process 200 for performing minimally invasive surgical procedures, according to an example embodiment. The sequence of steps depicted is for illustrative purposes only and is not meant to limit the method in any way as it is understood that the steps may proceed in a different logical order, additional or intervening steps may be included, or described steps may be divided into multiple steps, without detracting from the invention.

In step 205, the process includes providing a minimally invasive surgical device. As described above with respect to FIGS. 1-5, the device includes a needle 105 defining a hollow shaft 106 that extends from a first open end 107 to a second open end 108. The first end 107 of the needle is beveled to form a sharp point to puncture into skin. The second end 108 of the needle includes a hub 109 for mounting the needle onto a conventional syringe (not shown). The device further includes a guidewire 110 that is configured to safely allow entry into the uterine cavity by means of the Seldinger technique and at least one dilator 115 defining a tapered hollow shaft 116 that extends from a first open end 117 to a second open end 118. The device further includes a trocar assembly 125 comprising a cannula 135 defining a hollow tubular sleeve 136 that extends from a first open end 137 to a second open end 138 and an obturator 145 defining a hollow shaft 146 that extends from a first open end 147 to a second open end 148.

In step 210, the process includes inserting the first open end of the needle through a patient's skin and into a body cavity to create an opening 102 into a body cavity 101. In one embodiment, the first open end of the needle may be inserted into the body cavity using ultrasound guidance. In step 215, the process includes inserting a first end 111 of the guidewire 110 into the second open end 108 of the needle 105 such that the first end 111 of the guidewire 110 extends through the first open end 107 of the needle 105 into the uterine cavity 101 and a second end 112 of the guidewire 110 remains outside of a patient's body. In step 220, the process includes removing the needle from the body cavity such that the first end of the guidewire remains inside the body cavity and the second end of the guidewire remains outside of the patient's body.

In step 225, the process includes inserting the first open end 117 of the at least one dilator 115 over the second end 112 of the guidewire 110 and through the body cavity 101 to separate and dilate the diameter of the opening into the body cavity 101 made by the needle. In one embodiment, the process further includes successively advancing additional dilators of gradually increasing size over the second end of the guidewire and through the body cavity opening to increase the diameter of the opening into the body cavity 101 made by the needle. In step 230, the process includes removing the at least one dilator from the body cavity such that the first end of the guidewire remains inside the body cavity and the second end of the guidewire remains outside of the patient's body.

In step 235, the process includes inserting the first open end 147 of the hollow obturator 145 into the second open end 138 of the cannula 135 such that the first open end of the obturator protrudes from the first open end of the cannula to penetrate the patient's skin and thereby facilitate access to the body cavity. In step 240, the process includes passing the first open end 117 of the hollow obturator and the first open end 137 of the cannula 135 over the second end 112 of the guidewire and through the opening 102 into the body cavity 101. For better illustration, FIG. 12 is a perspective view of the obturator being guided into the body cavity using the guidewire, as in the Seldinger technique.

In step 245, the process includes removing the obturator and the guidewire from the body cavity such that the first open end of the cannula remains inside the body cavity and the second open end of the cannula remains outside of the patient's body to provide a portal to the body cavity.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

I claim:

1. A method for performing minimally invasive uterine or fetal surgical procedures, comprising:
   a) providing a device comprising:
      a hypodermic needle defining a hollow shaft that extends from a first open end to a second open end;
      a guidewire defining a first end and a second end; and
      a trocar assembly comprising:
         a cannula defining a hollow tubular sleeve that extends from a first open end to a second open end, wherein the cannula further comprises one or more flanges extending away from an exterior of the cannula, the one or more flanges configured for holding the cannula in place within an interior of a uterus; and
         a hollow obturator defining a shaft that extends from a first open end that is tapered to a second open end, wherein the hollow obturator is located within the cannula, wherein the hollow obturator comprises a first disc with a first diameter coupled to the second open end of the hollow obturator and a second disc having a second diameter greater than the first diameter, located distally from the first disc;
   b) inserting the first open end of the needle through a patient's skin and into an amniotic cavity so as to create an opening;
   c) inserting the first end of the guidewire through the second open end of the needle and into the amniotic cavity;
   d) removing the needle from the amniotic cavity such that the first end of the guidewire remains inside the amniotic cavity and the second end of the guidewire remains outside of the patient's body;
   e) inserting the first open end of the obturator into the second open end of the cannula such that the first open end of the obturator protrudes from the first open end of the cannula;
   f) passing the first open end of the obturator and the first open end of the cannula over the second end of the guidewire and inserting the trocar assembly into the amniotic cavity using the guidewire as a guide; and
   g) removing the obturator and the guidewire from the uterine cavity such that the first open end of the cannula remains inside the amniotic cavity and the second open end of the cannula remains outside of the patient's body to provide a portal to the amniotic cavity.

2. The method of claim 1, wherein the needle comprises an 18-gauge hypodermic needle having an outer diameter of 1.2 mm.

3. The method of claim 2, wherein the first open end of the needle is inserted into the amniotic cavity using ultrasound guidance.

4. The method of claim 3, wherein the hollow tubular sleeve of the cannula comprises an outer diameter of 5 mm.

5. The method of claim 4, wherein the method further comprises advancing at least one dilator successively over the second end of the guidewire and into the amniotic cavity to gradually increase a diameter of the opening.

* * * * *